(12) United States Patent
Van Wegen et al.

(10) Patent No.: US 9,606,096 B2
(45) Date of Patent: Mar. 28, 2017

(54) METHOD AND APPARATUS FOR DETECTING CRACKS IN EGGSHELLS

(71) Applicant: Moba Group B.V., Barneveld (NL)

(72) Inventors: Edwin Van Wegen, Barneveld (NL); Josse De Baerdemaeker, Leuven (BE); Bart Kemps, Leuven (BE); Jeroen Evert Jan Brunnenkreef, Barneveld (NL); Bart De Ketelaere, Leuven (BE)

(73) Assignee: MOBA GROUP B.V., Barneveld (NL)

( * ) Notice: Subject to any disclaimer, the term of this patent is extended or adjusted under 35 U.S.C. 154(b) by 0 days.

(21) Appl. No.: 14/412,616

(22) PCT Filed: Jul. 5, 2013

(86) PCT No.: PCT/NL2013/050508
§ 371 (c)(1),
(2) Date: Jan. 2, 2015

(87) PCT Pub. No.: WO2014/007637
PCT Pub. Date: Jan. 9, 2014

(65) Prior Publication Data
US 2015/0219611 A1    Aug. 6, 2015

(30) Foreign Application Priority Data
Jul. 5, 2012 (EP) .................................... 12004999

(51) Int. Cl.
*G01N 33/08* (2006.01)
*A01K 43/00* (2006.01)
(Continued)

(52) U.S. Cl.
CPC .............. *G01N 33/08* (2013.01); *A01K 43/00* (2013.01); *G01N 21/13* (2013.01); *G01N 21/55* (2013.01);
(Continued)

(58) Field of Classification Search
CPC ...... G01N 33/08; G01N 33/085; G01N 21/55; G01N 21/13; G01N 21/95; G01N 2201/06113; G01N 2201/12; A01K 43/00
(Continued)

(56) References Cited

U.S. PATENT DOCUMENTS 3,067,605 A * 12/1962 Bliss ...................... A01K 43/00
                                                73/12.09
5,131,274 A *  7/1992 Schouenborg ......... G01N 33/08
                                                209/510
(Continued)

OTHER PUBLICATIONS

International Search Report for PCT/NL2013/050508 dated Oct. 31, 2013.
(Continued)

*Primary Examiner* — Laura Martin
*Assistant Examiner* — Rose M Miller
(74) *Attorney, Agent, or Firm* — Marvin Petry; Stites & Harbison PLLC

(57) ABSTRACT

This invention relates to a method and an apparatus for characterizing eggshells of eggs, the eggs being supported, comprising: —deforming the eggshell, —scanning the eggshell with a laser beam of a Self Mixing Laser Vibrometer (SMLV) with scanning signals, whereby a reflection light signal of reflection light is obtained, —processing scanning signal and the reflection signal with the SMLV, whereby a mixed signal with crack information is obtained, —during scanning moving the eggs relative to the SMLV, —comparing the signals with preset criteria and characteristics of such eggs, whereby comparative data are obtained, and —characterizing the eggshells on the basis of the comparative data.

18 Claims, 3 Drawing Sheets

Figure 1:
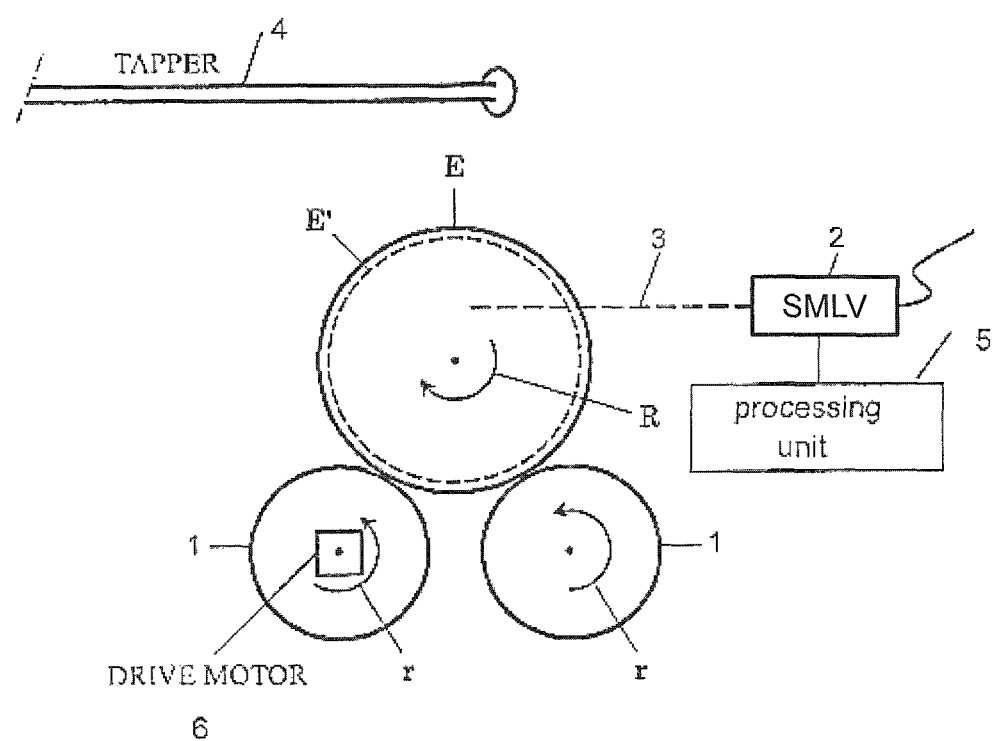

(51) Int. Cl.
  *G01N 21/95* (2006.01)
  *G01N 21/13* (2006.01)
  *G01N 21/55* (2014.01)

(52) U.S. Cl.
  CPC ..... *G01N 21/95* (2013.01); *G01N 2201/0438* (2013.01); *G01N 2201/06113* (2013.01); *G01N 2201/12* (2013.01)

(58) Field of Classification Search
  USPC .......................................... 73/579, 595, 643
  See application file for complete search history.

(56) References Cited

U.S. PATENT DOCUMENTS

| | | | |
|---|---|---|---|
| 5,426,977 A * | 6/1995 | Johnston | G01H 13/00 73/579 |
| 5,615,777 A | 4/1997 | Weichman et al. | |
| 5,696,325 A | 12/1997 | Coucke et al. | |
| 5,728,939 A | 3/1998 | Moayeri | |
| 2002/0189321 A1* | 12/2002 | De Baerdemaeker | A01K 43/00 73/12.14 |
| 2007/0030669 A1 | 2/2007 | Soest | |
| 2013/0283894 A1 | 10/2013 | De Ketelaere et al. | |

OTHER PUBLICATIONS

Written Opinion of the International Searching Authority for PCT/NL2013/050508 dated Oct. 31, 2013.

Pawan Kumar Shrestha: "Self-Mixing Diode Laser Interferometry", Thesis, submitted to the University of Waikato, New Zealand, (Feb. 1, 2010), XP055086356, Retrieved from the Internet: URL:http://researchcommons.waikato.ac.nz/h_andle/10289/5910 [retrieved on Oct. 31, 2013].

B. De Ketelaere et al: "Eggshell Crack Detection based on Acoustic Resonance Frequency Analysis", Journal of Agricultural Engineering Research, vol. 76, No. 2, (Jun. 1, 2000), pp. 157-163.

* cited by examiner

METHOD AND APPARATUS FOR DETECTING CRACKS IN EGGSHELLS

The present invention relates to a method and an apparatus for characterizing eggshells of eggs.

Such a method and apparatus are known from Pawan Lumar Shrestha, "Self-Mixing Diode Laser Interferometry", Waikato University, Hamilton, New Zealand, February 2010, hereinafter called Shrestha. More particularly, it is described for the method how cracks in eggshells of eggs are detected and determined, namely by, positioning an egg, located on rollers, with the crack directly opposite a laser vibrometer, while each time, with the rollers, a next fixed observation position of an egg can be selected, bringing the egg into resonance with focused speaker sound using tones between 400 Hz and 17 kHz, measuring the resonance signal with a laser vibrometer whereby both a signal for the course of the amplitude and a signal for the course of the frequency are obtained with the aid of Fourier analysis.

In addition to the laser vibrometer mentioned, in particular, the principle of 'self mixing' realised by a Self Mixing Laser Vibrometer (SMLV) is discussed at length.

As is elucidated in detail in this document, the resonance frequency signal is obtained with the aid of one of the reconstruction models developed to that end, based on wave mechanics known to those skilled in the art.

However, in this document, no application or solution is offered in case large numbers of eggs are to be checked for cracks, as is the case, for instance, in egg sorters of which an example is shown in EP738888.

It has appeared that a type of signal and the associated processing as described by Shrestha are not suitable for industrial applications, namely, neither for determining cracks for large numbers of eggs in a short time, nor for determining, for instance, the location of a crack on the eggshell. Also, no clear criterion is given or applied for making the choice of yes/no crack, nor for any further characterization of such a crack.

In order to remedy such a shortcoming, according to the present invention, there is provided a method for characterizing eggshells of eggs, the eggs being supported, comprising, deforming at least a first part S1 of the eggshell of such an egg, scanning with a laser beam of a Self Mixing Laser Vibrometer (SMLV) with scanning signals said first part S1, or an at least second part S2 of said eggshell with laser source light from a laser source having wavelengths $\lambda$, with $100<\lambda<1500$ nm, whereby at least a single reflection light signal of reflection light is obtained, processing said scanning signal and said reflection signal with said SMLV, whereby a mixed signal is obtained with amplitude A(t) or quantity A'(t) derived therefrom, whereby crack information is obtained, during scanning moving the eggs relative to the SMLV, in said processing, comparing said signals with preset criteria and characteristics of such eggs, whereby comparative data are obtained, and characterizing said eggshells on the basis of said comparative data whereby characteristics of eggshell conditions of substantially the whole eggshell are obtained.

It has appeared that with the method according to the invention, the behavior of eggshell parts set into motion can be monitored in a very simple manner.

More particularly, according to the method of the invention as indicated hereinabove, eggs are briefly deformed. Such a deformation will spread through the egg and especially over the eggshell and thereby cause a vibration of the egg as a whole. While according to the above known methods these vibrations are monitored for relatively long periods of time after excitation, namely the resonance in the detector according to EP738888 and the resonance of the egg body according to Coucke and the methodologies derived therefrom, according to the present invention, the signals as obtained during deformation are analysed. The then occurring and observable behavior of the respective part of the eggshell differs considerably from the resonance behavior mentioned.

Further, embodiments of the method can have the characteristic that the mixed signal is obtained with the aid of Doppler shift upon movement of the eggs;

that the processing of the mixed signal A(t) comprises determining the number of intensity fluctuations A(t(i)) at points in time t(i) immediately after said deformation;

that the processing of the mixed signals A(t) comprises determining the number of saltatory intensity fluctuations A(t(i)) at points in time t(i) immediately after said deformation;

that of said intensity fluctuations, the first signal derivative dA/dt, or a quantity [dA/dt]' derived therefrom, is determined;

that the processing of the mixed signal A(t) further comprises determining, of A(t) or a derivative A'(t), zero axis crossings at points in time t(i) immediately after said deformation, wherein A(t(i))=0, or A'(t(i))=0; that the mixed signal is processed for the period 0<t<1 ms after said deformation which starts at t(0);

that processing takes place preferably in the period 50<t<800 μs, more particularly 100<t<700 μs;

that said first part S1 comprises a location on the equator of such an egg; that said first part S1 comprises a location at at least one of the ends of such an egg;

that it holds for said second part that S2=S1;

that said second part S2 comprises a pattern of rings on the egg surface, substantially parallel to the equator; and/or that such an egg rotates at least during scanning.

Furthermore, the present invention provides a method for sorting eggs on the basis of well-defined characteristics, wherein at least eggshell characteristics according to one of the preceding claims are comprised.

Regarding further details of prior art methods that come close to the method according to the present invention, in addition to the above discussed Shrestha, the following is noted.

According to the method and apparatus from EP 738888, eggs located on rotating rollers of an endless roller conveyor are ring-wise tapped along at least two rings by a tapper-detector combination specifically developed for that purpose. Each tap by a ball locally on the egg also produces a sound signal in the housing of the detector or vibration sensor. This signal provides information on the corresponding local eggshell condition, more particularly on, for instance, the presence or absence of a crack in the eggshell in the surroundings of the tapping location. The combination of all taps for each egg in such a tapping procedure thus offers information on practically the whole eggshell. This information is one of the criteria that lead to a sorting decision about such an egg.

More particularly, the information that is thus obtained is indirect, namely via the vibration of the ball in the housing of the vibration sensor. However, such a vibration sensor itself, too, needs to be continuously monitored and tested for its own vibratory behavior. This is especially necessary in respect of, for instance, wear or pollution of the parts constituting this sensor.

It is clear that, basically, for determining the location practically the entire surface of the eggshell should be scanned with such a tapping procedure.

A wholly different manner for establishing cracks utilizes vibration or excitation of the egg as a whole. For details of the thus obtained resonance behavior of eggs, reference is made to "Assessment of some physical quality parameters of eggs based on vibration analysis", P. Coucke, Catholic University of Louvain, March 1998 (hereinafter referred to as Coucke), where it is extensively described how an egg that is brought into resonance, more particularly the eggshell thereof, behaves. Such behavior is characterized by so-called resonance modes.

Monitoring and measuring such resonance behavior is for instance utilized in U.S. Pat. No. 5,696,325 and in EP1238582.

In U.S. Pat. No. 5,696,325, a test procedure for crack in eggshells is described. Here, a ball dropping on the egg causes mechanical vibrations of the egg as a whole. These vibrations are the vibrations described in Coucke. With a transducer, these mechanical vibrations which are physically described as acoustic vibrations, are converted into electrical signals, suitable for further analysis.

Unlike in EP738888 above, in EP1238582 a tapping procedure is described whereby, in essence, with a single tap the egg as a whole is set into vibration as described by Coucke. The resulting sound effect is detected by a microphone in the vicinity of the egg. Deviations in resonance effects, more particularly the resonance modes, can be detected and provide information on possible cracks in the eggshell. Clearly, this information basically concerns the condition of the egg as a whole. However, it appeared not to be possible to obtain reliable data about specific locations of cracks, nor about the nature or the severity of such a crack.

It is further noted that, unlike for the vibration behavior according to EP738888 or Coucke, where measurement takes place a shorter or longer time after excitation, with the apparatus according to the invention, the transition between 'in rest' and 'setting into motion' of said part of the eggshell is monitored in detail. It has appeared that such transitional behavior can be accurately monitored with laser light reflected by the egg. It has been established here that the transition behavior of broken and intact eggs differs considerably. It will be clear to those skilled in the art that such differences are highly suitable as selection criteria.

Regarding the prior art apparatuses that come close to an apparatus according to exemplary embodiments of the present invention, further details have been given hereinabove, with specific reference to Shrestha, EP738888, U.S. Pat. No. 5,696,325, EP1238582 and Coucke.

An apparatus which in a simple, direct and unambiguous manner gives detailed information on conditions and characteristics of such an eggshell surface as a whole, more particularly an apparatus whereby in a very short period of time large quantities of eggs are tested for cracks and their further characteristics, is by no means achieved with the above techniques.

In order to provide a solution for the above shortcoming, the invention provides an apparatus for detecting cracks in the shells of eggs, the eggs being supported with carriers, comprising:

an exciter for deforming a first part S1 of the eggshell of such an egg, a Self Mixing Laser Vibrometer (SMLV) for scanning with scanning signals said first part S1 or at least a second part S2 of such an eggshell with laser source light having wavelengths $\lambda$, with $100<\lambda<1500$ nm, whereby a reflection signal is obtained, wherein the SMLV processes the scanning signals and the reflection signals into mixed signals with amplitude $A(t)$, or quantity $A'(t)$ derived therefrom, and a processing unit for processing the mixed signals whereby eggshell information is obtained, a driving device for moving the carriers relative to the SMLV, wherein the processing unit is further configured for:

comparing the mixed signals with preset criteria and characteristics of such eggs, whereby comparative data are obtained, and characterizing said eggshells on the basis of said comparative data whereby eggshell characteristics of eggshell conditions are obtained.

First of all, what is thus achieved in a suitable manner is that deformations over the entire egg surface can be scanned in a contactless manner. Transfer of dirt and pathogens between eggs by one and the same scanner is definitively prevented and obviated so that stricter hygiene requirements can be met.

A further advantage is the compactness of this apparatus many specimens of which can be provided along the sorting tracks of a sorting machine. Another advantage that can be mentioned is that for such laser detection, quite unlike the above mentioned mechanical or acoustic detection, wear is virtually completely eliminated.

An apparatus for obtaining and processing such reflection light is known from, for instance, Giuliani et al., Laser diode self-mixing technique for sensing applications, Journal of Optics A: Pure and Applied Optics, 4 (2002) 283-294, where it is described how measurements of vibrations of objects can be carried out. What is essential then is the circumstance that use is made of the Doppler shift of the reflected signals upon rotation of an exposed object. For further characterization and processing of such signals, reference is made to the cited article. As already mentioned hereinabove, this measuring technique is denoted with SMLV. In addition, the abbreviation 'IN' will be used as abbreviation for 'Laser Vibrometer'. To those skilled in this field of technology, the operation and the use of an LV is generally known.

A further embodiment of the invention can comprise:

rollers for supporting such an egg at at least two circumferential positions thereof, and a drive for rotating the rollers, whereby in consequence thereof a supported egg rotates.

As explained hereinabove at length, it is known from for instance EP738888 and from EP1238582 to excite the eggshells with the aid of tappers. Not only are the requirements set for such tappers high and very specific, but also the installation thereof for thus obtaining suitable signals for further processing requires much expert setting experience.

In order to remedy such laboriousness, the present invention furthermore provides an apparatus for sorting eggs according to at least the presence of cracks, whereby the cracks are detected and characterized with the apparatus and the method according to any one of the above-mentioned features.

It is further noted that the use of techniques whereby light is used for detecting cracks in eggshells is known per se. Generally known is the traditional technique called candling, as known for instance from US2007030669. This techniques does not relate in any manner to eggs set into vibration; further it is a condition that the eggs are irradiated. For scanning an egg with a laser beam, reference is made to U.S. Pat. No. 5,615,777 in which a laser beam with a specific lighting pattern is used for visualizing cracks in eggshells with laser light exiting at angles. However, it has appeared that the reliability of this method is insufficient to arrive at suitable results in sorting.

Furthermore, the present invention provides an apparatus for sorting eggs according to at least the presence of cracks, whereby the cracks are detected and characterized with the apparatus and method according to any one of the preceding claims.

Figure 2A:
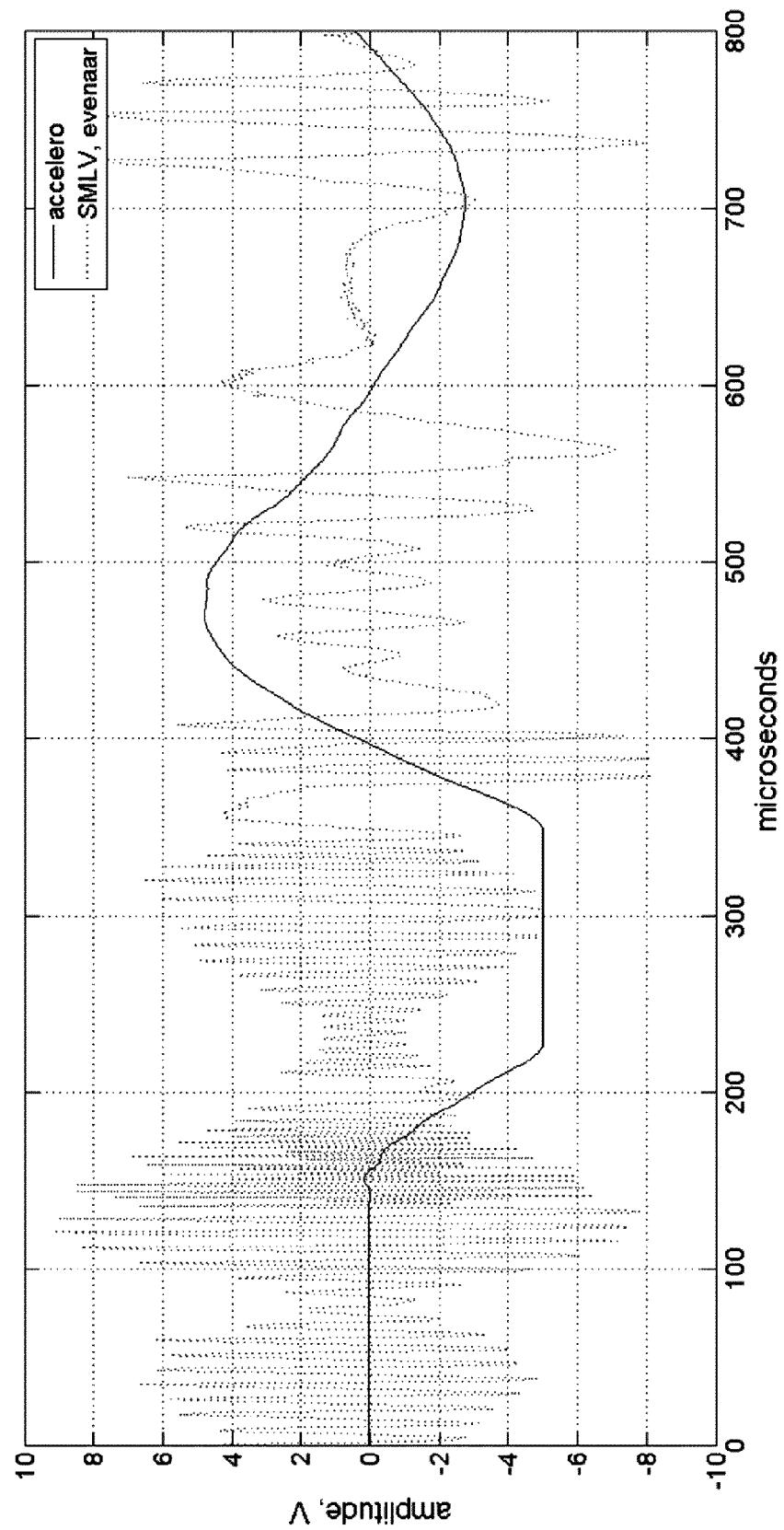
Figure 2B:
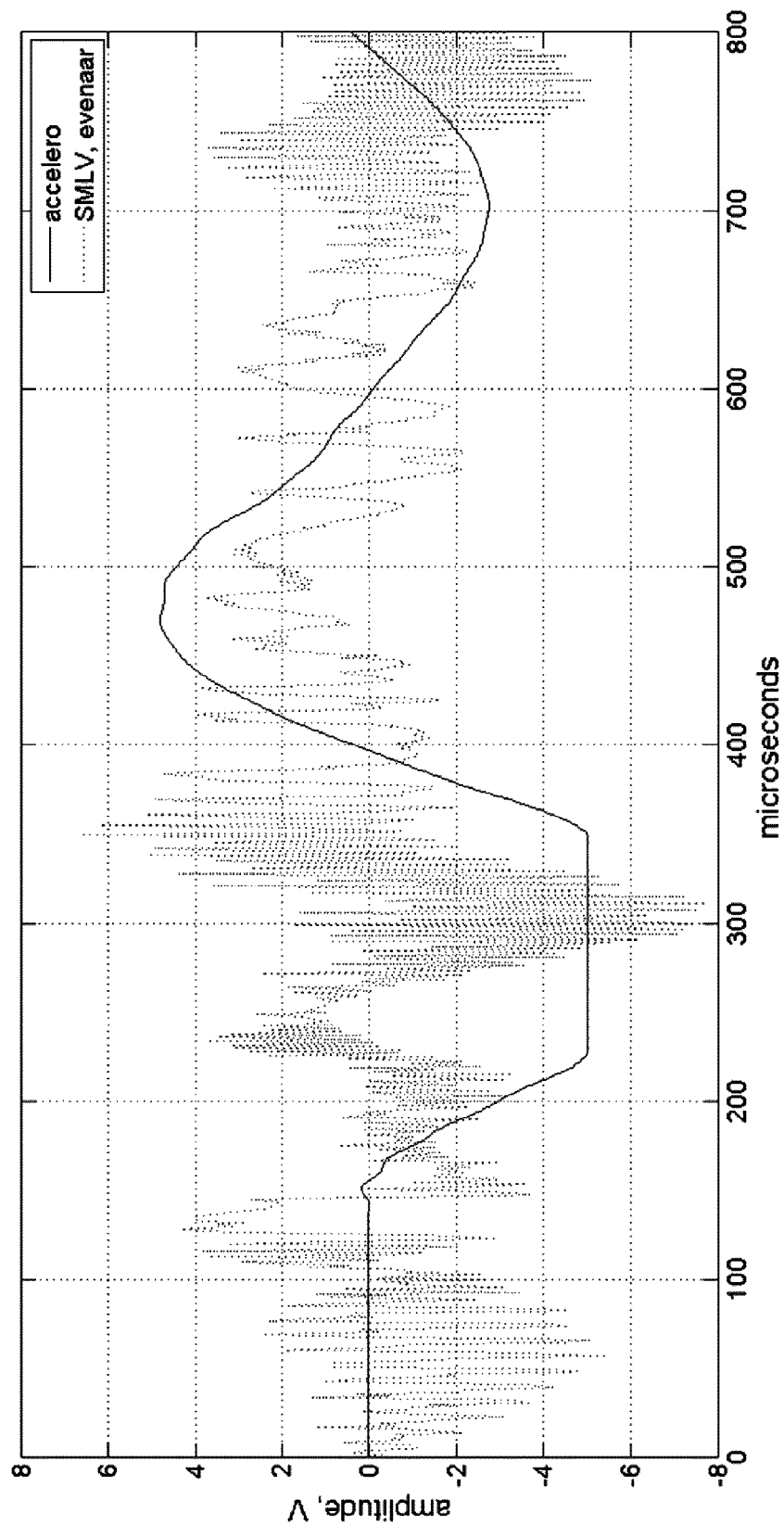

Further details of the method and apparatus according to this invention are elucidated on the basis of a drawing, wherein FIG. 1 shows a schematic side view of an exemplary embodiment of an apparatus, and wherein FIGS. 2A,B show examples of signal shapes which have been obtained and are used, wherein FIG. 2A gives the signal shape of a thus excited intact egg, and wherein FIG. 2B gives the signal shape of a thus excited broken egg.

In FIG. 1, an egg E is located on rollers 1. These rollers 1 rotate in a direction r indicated with an arrow with arrowhead. It will be clear that at least one of the rollers must be driven externally, for instance by means of a motor 6, so that with the egg E on both rollers, and with a rotating egg E in the direction of R, also indicated with an arc with arrowhead, the second roller 1 will rotate.

An SMLV detector 2 is arranged near this egg E, and will, by means of the above indicated optical mixed signal of exposure light and reflection light at a light spot, be able to monitor occurring and developing deformations and movements. Upon rotation of such an egg E, for instance locations along a ring will be followed. It will be clear to those skilled in the art that depending on directions and speeds, a desired number of locations are observed. In the exemplary embodiment according to FIG. 1, schematically, a beam 3 is represented in a random plane through such an egg E. If so desired, the direction for this plane can be oblique or perpendicular, and patterns of locations of points of impact for the laser beam can be set. For instance, for an egg surface, a combination can be set of the meridian or parallel with ring near or with the point of impact on an end.

It will be clear to those skilled in the art that upon movement of such eggs, Doppler shift of the reflection signal is obtained. The conditions for simple processing according to the SMLV principle referred to above are then suitably met. This movement can be the translation or passing of an egg, or eggs in a long row, on for instance a conveyor, rotating of such an egg on the said carriers, i.e., the rollers, or a combination of passing and rotating.

Furthermore, in FIG. 1, it is schematically indicated with broken line E' that the egg E has been set into vibration by a tapper 4 whereby the surface upon resonance follows a wave motion.

It will be clear to those skilled in the art that such a manner of having an egg E rotate is suitable both when applied in a test setup and in a roller sorter where similar rollers are utilized, for instance a roller sorter as mentioned in EP1238582. It will be clear to those skilled in the art that the rollers in a sorter can be driven in various manners, for instance by rolling them over a support belt. In case of examination of a single egg situated on two successive rollers, driving one of these rollers can suffice.

In this exemplary embodiment, it is represented how an egg E can be deformed and set into vibration by tapping the egg E using tapper 4. In this field of technology, it is known to those skilled in the art in what manner this can be effected. Again, for an example of this, reference is made to the exciter or tapper according to EP1238582. The exemplary embodiment of an apparatus illustrated in FIG. 1 is also provided with a processing unit 5 that, as referenced above and described in greater detail below, is configured for processing the optical mixed signal of exposure light and reflection light to obtain eggshell information, including comparing the mixed signal with preset criteria and characteristics of eggs to obtain comparative data, and characterizing eggshells based on the comparative data to obtain eggshell characteristics of eggshell conditions.

In FIGS. 2A,B are represented the signal shapes which are obtained upon deformation of a shell part of an intact egg and a broken egg, respectively.

More particularly, these signal shapes are the result of tapping, and thereby deforming, at the equator, and scanning with a laser beam, also at the equator. For the situation of the broken egg in FIG. 2B, a crack was provided likewise at the equator. The laser used is a continuous laser with light of a wavelength $\lambda$ of 655 nm.

The examined eggs are located on rotating rollers and have a speed of 0.67 revolution/s.

Tapping of an egg and thereby deforming it and setting it into vibration is carried out with a tapper substantially according to the model as described in EP1238582.

FIG. 2A is a signal diagram where two signals as mentioned hereinabove and obtained with the SMLV principle are represented:

the mixed signal obtained from a rotating egg is converted into an electrical voltage V, and can be recognized by the high frequency voltage fluctuations;

the second line begins horizontally and then passes the 0-line three times. The diagram is a record of such a voltage gradient over a time period of 0.8 ms, or also 800 μs.

The second line or curve is a representation of the signal representing the movement of the tapper. This signal is obtained with an accelerometer of the type MODEL352B70, of PCB-Piezotronics, mounted on the tapper. The signal is a representation of the acceleration which the tapping end of the tapper experiences. More particularly, the start of tapping is marked at 150 μs after the start.

The subsequent negative voltage values show the deceleration of the tapper, i.e., the 'denting' or deformation of the tapping location of the eggshell, with the deceleration constantly increasing. The subsequent horizontal section has been omitted in the processing of the signal by means of generally known signal limitation. With the subsequent visible rising line, deceleration diminishes again and returns to 0. That moment, at approximately 400 μs, is the moment at which deformation stops and the tapper swings back, away from the egg.

The above-mentioned first signal is a representation of the intensity that the scanning light together with the reflection light results in.

More in detail, these are very rapidly changing intensities resulting mainly from distance changes with phase jumps and Doppler shift in the light signal that are caused by the eggshell surface part bouncing to and fro, which interplay propagates over the entire eggshell. In this FIG. 2A, for an intact egg this is a regularly changing and gradually increasing and decreasing intensity.

In FIG. 2B, a similar record is made for a broken egg. While the second curve in this FIG. 2B is approximately equal to that in FIG. 2A, the second signal has completely different characteristics. More particularly, far more intensity fluctuations occur while the increases and decreases are considerably greater because the reflecting shell part has more freedom to move and upon deformation will deflect more and hence 'bounce' more.

The differences in the intensities of the reflection signals obtained upon deformation of an intact egg and a broken egg, respectively, are considerable. Such differences enable in a very suitable manner to make a distinction between intact and broken eggs, more particularly the distinction between severity, nature, and location of such cracks.

One manner of characterizing these differences is to compare the intensity fluctuations. A derivative measure is to measure the number of zero-axis crossings of this first signal and to compare it with a standard for an intact egg.

In the foregoing, it has been elucidated how locations where the egg, more particularly the eggshell, is deformed are selected, and where deformations and movements are recorded and monitored. These locations are indicated with S1 and S2, respectively the location for deforming and, by extension, for monitoring. It will be clear to those skilled in the art that many patterns and combinations are possible whereby substantially deformations and movements over the entire egg surface can be monitored and examined, with possibilities S1=S2, rings, lines, degrees of longitude and latitude, pointed end and wide end, and, as clearest location, that of the equator.

It will be clear to those skilled in the art that small modifications in the above disclosure are understood to fall within the scope of the appended claims.

For instance, products having properties similar to those of eggs can be monitored and examined with the present method and apparatus.

The invention claimed is:

1. A method for detecting cracks in and characterizing eggshells of eggs, the method comprising:
   deforming a first surface aspect of an eggshell of an egg that is supported;
   during a time period t, where 0 μs<t<1000 μs, immediately after t(0), where t(0) is a point in time at which deformation of the first surface aspect of the eggshell is initiated, using a laser beam of laser source light having a wavelength λ, with 100 nm<λ<1500 nm, from a laser source of a Self Mixing Laser Vibrometer (SMLV) to scan the first surface aspect of the eggshell or a second surface aspect of the eggshell with a scanning signal while concurrently moving the egg to obtain a reflection light signal of reflection light at the surface aspect of the eggshell that is scanned with the scanning signal;
   processing the scanning signal and the reflection light signal with the SMLV to obtain a mixed signal representing intensities of exposure light and reflection light at the surface aspect of the eggshell that is scanned with the scanning signal and indicative of existence of any cracks in the eggshell;
   analyzing the mixed signal with respect to preset criteria representative of eggshell characteristics to obtain comparative data indicative of conditions of the eggshell; and
   determining characteristics of substantially an entirety of a surface of the eggshell based on the comparative data indicative of conditions of the eggshell.

2. A method according to claim 1, wherein the mixed signal is obtained according to a Doppler shift of the reflection light signal that occurs upon movement of the egg.

3. A method according to claim 1, wherein the mixed signal is a voltage signal having an amplitude gradient A(t), and further comprising processing the mixed signal to determine a quantity of intensity fluctuations A(t(i)) that occur in the amplitude gradient A(t) at points in time t(i) immediately after t(0) as an indication of existence of any cracks in the eggshell.

4. A method according to claim 3, further comprising determining a first signal derivative dA/dt of the intensity fluctuations A(t(i)) that occur in the amplitude gradient A(t) or a quantity [dA/dt'] derived therefrom.

5. A method according to claim 1, wherein the mixed signal is a voltage signal having an amplitude gradient A(t), and further comprising processing the mixed signal to determine a quantity of saltatory intensity fluctuations A(t(i)) that occur in the amplitude gradient A(t) at points in time t(i) immediately after t(0) as an indication of existence of any cracks in the eggshell.

6. A method according to claim 1, wherein the mixed signal is a voltage signal having an amplitude gradient A(t), and further comprising processing the mixed signal to determine zero-axis crossings that occur in the amplitude gradient A(t) or a derivative of the amplitude gradient A'(t) at points in time t(i) immediately after t(0).

7. A method according to claim 1, further comprising processing a portion of the mixed signal representing the time period t immediately after t(0).

8. A method according to claim 7, wherein the portion of the mixed signal occurs within a period 50 μs<t<800 μs after t(0) represented in the mixed signal.

9. A method according to claim 1, wherein the first surface aspect of the eggshell comprises a location on an equator of the egg.

10. A method according to claim 1, wherein the first surface aspect of the eggshell comprises a location at at least one end of the egg.

11. A method according to claim 1, wherein the laser beam from the laser source of the SMLV is used to scan the first surface aspect of the eggshell.

12. A method according to claim 1, wherein the laser beam from the laser source of the SMLV is used to scan the second surface aspect of the eggshell, and wherein the second surface aspect of the eggshell comprises a pattern of rings on the surface of the eggshell that is substantially parallel to an equator of the egg.

13. A method according to claim 1, wherein concurrently moving the egg while using the laser beam from the laser source of the SMLV is used to scan the first or second surface aspect of the eggshell comprises rotating the egg.

14. A method for sorting eggs, the method comprising:
   determining characteristics of substantially an entirety of a surface of an eggshell of each of a plurality of eggs by performing the method of claim 1 for each of the plurality of eggs; and
   sorting the plurality of eggs based on at least the characteristics of substantially the entirety of the surface of the eggshell determined for each of the plurality of eggs by performing the method claim 1 for the egg.

15. A method for sorting eggs, the method comprising:
   determining characteristics of substantially an entirety of a surface of an eggshell of each of a plurality of eggs by performing the method of claim 1 for each of the plurality of eggs; and sorting the plurality of eggs based on at least the existence of any cracks in the eggshell of each of a plurality of eggs as indicated by the mixed signal obtained for the egg by performing the method claim 1 for the egg.

16. An apparatus for detecting cracks in and characterizing shells of eggs, the apparatus comprising:
- an exciter for deforming a first surface aspect of an eggshell of an egg that is supported by a carrier;
- a driving device for moving the carrier;
- a Self Mixing Laser Vibrometer (SMLV) for scanning the first surface aspect of the eggshell or a second surface aspect of the eggshell with a scanning signal using a laser beam of laser source light having a wavelength $\lambda$, with 100 nm<$\lambda$<1500 nm, from a laser source of the SMLV while the driving device is concurrently moving the carrier to obtain a reflection light signal of reflection light and processing the scanning signal and the reflection light signal to obtain a mixed signal representing intensities of exposure light and reflection light at the surface aspect of the eggshell that is scanned with the scanning signal and indicative of existence of any cracks in the eggshell; and
- a processing unit for analyzing the mixed signal with respect to preset criteria representative of eggshell characteristics to obtain comparative data indicative of conditions of the eggshell and determining characteristics of substantially an entirety of a surface of the eggshell based on the comparative data indicative of conditions of the eggshell.

17. An apparatus according to claim 16,
wherein the carrier comprises rollers for supporting the egg at at least two circumferential positions of the egg, and
wherein the driving device is configured to move the carrier by rotating the rollers, thereby causing rotation of the egg supported by the rollers.

18. An apparatus according to claim 16, further comprising a sorter for sorting the egg among a plurality of eggs according to at least the existence of any cracks in the eggshell of the egg indicated by the mixed signal obtained for the egg by the SMLV.

* * * * *